United States Patent
Götz et al.

(10) Patent No.: US 6,559,343 B1
(45) Date of Patent: May 6, 2003

(54) PROCESS FOR PRODUCING 2,2,4,4-TETRA-SUBSTITUTED 1,3,5-CYCLOHEXANETRIONES

(75) Inventors: Roland Götz, Neulussheim (DE); Norbert Götz, Worms (DE); Matthias Witschel, Ludwigshafen (DE); Michael Rack, Heidelberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/979,990
(22) PCT Filed: May 19, 2000
(86) PCT No.: PCT/EP00/04567
§ 371 (c)(1), (2), (4) Date: Nov. 29, 2001
(87) PCT Pub. No.: WO00/75095
PCT Pub. Date: Dec. 14, 2000

(30) Foreign Application Priority Data

Jun. 2, 1999 (DE) .......................... 199 25 145

(51) Int. Cl.$^7$ .................. C07C 45/50; C07C 45/54; C07F 7/04
(52) U.S. Cl. ............ 568/343; 568/347; 568/351; 568/353; 556/436
(58) Field of Search ................ 568/343, 347, 568/351, 353; 556/436

(56) References Cited

FOREIGN PATENT DOCUMENTS

EP 283 152 10/1988

OTHER PUBLICATIONS

Chem.Ber. (1959) (92) 2033–7,Murin et al.
J.Org.Chem(1961)vol.26,4340–4344,Hasek et al.
J.Org.Chem.(1962)vol.27,3106–3111,Hasek et al.
LiebigsAnn.Chem.,1828–1846 (1979) Himbert et al.
J.Org.Chem.1996,61,73–81,Padwa et al.
Chem.Abst. 601, vol.92,1980.
Chem. Abst. 2211, vol. 84 (1971).
Synthetic Com,19 (18), 3241–3247 (1989)Benbakkar et al.
J.Org.Chem.vol.46,1972,59–71,Ainsworth et al.
J.Org.Chem. (1961)vol. 26, 700–704,Hasek et al.

*Primary Examiner*—Johann Richter
*Assistant Examiner*—Sikarl A. Witherspoon
(74) *Attorney, Agent, or Firm*—Keil & Weinkauf

(57) ABSTRACT

Process for the preparation of 2,2,4,4-tetrasubstituted 1,3,5-cyclohexanetriones of the formula I,

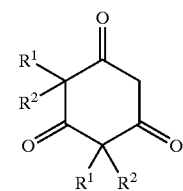

by reaction of a cyclobutane-1,3-dione of the formula II

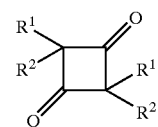

with an O or N nucleophile and a silylating reagent, and subsequent acetylation and cyclization.

22 Claims, No Drawings

PROCESS FOR PRODUCING 2,2,4,4-TETRA-SUBSTITUTED 1,3,5-CYCLOHEXANETRIONES

This application is a 371 of PCT/EP00/04567 filed May 19, 2000, now WO 00/75095, published Dec. 12, 2000.

The present invention relates to a process for the preparation of 2,2,4,4-tetrasubstituted 1,3,5-cyclohexanetriones of the formula I.

2,2,4,4-Tetrasubstituted 1,3,5-cyclohexanetriones of the formula I are used as intermediates for the preparation of herbicidally active compounds, such as described, for example, in EP-B 283 152.

Processes for their preparation are therefore of particular interest.

To date, the following syntheses are known as processes for the preparation of 2,2,4,4-tetrasubstituted 1,3,5-cyclohexanetriones:

1. The reaction of 2,4,6-trihydroxyacetophenone with an excess of methyl iodide and sodium methanolate and subsequent deacetylation by means of hydrochloric acid. The total yield of 2,2,4,4-tetramethyl-1,3,5-cyclohexanetrione (based on 2,4,6-trihydroxyacetophenone) is 37%. (EP-B 283 152).

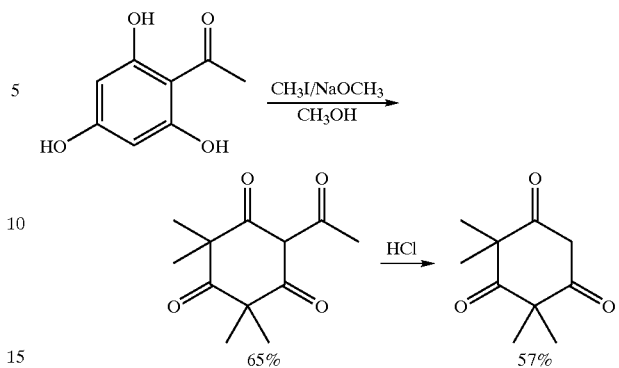

2. Starting from dimethyl acetonedicarboxylate, dimethyl tetra-C-methylacetonedicarboxylate was obtained by methylation, and this was converted into the dicarboxylic acid methyl ester chloride and then methylated with dimethylcadmium. The methyl 2,2,4,4-tetramethyl-3,5-dioxohexanecarboxylate obtained was cyclized in the presence of sodium methanolate. The total yield (based on dimethyl acetonedicarboxylate) is 0.01% (Chem. Ber. 92, 2033 (1959)).

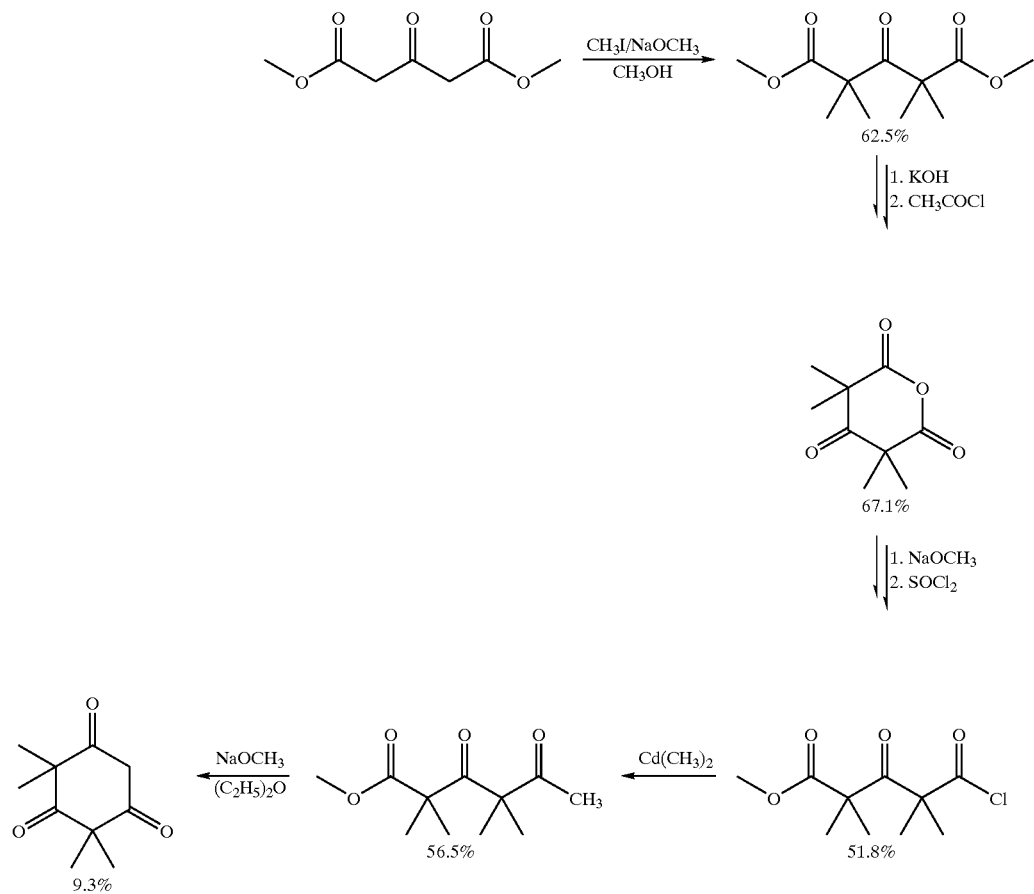

3. Ethyl 2,4,4-trimethyl-3-oxo-pentanecarboxylate was converted into the silyl enol ether at −78° C., acetylated in the presence of ZnCl$_2$ and then cyclized in the presence of lithium diisopropylamide. The total yield (based on ethyl 2,4,4-trimethyl-3-oxo-pentanecarboxylate) is 50% (M. Benbakkar et al., Synth. Commun. 19 (18) 3241).

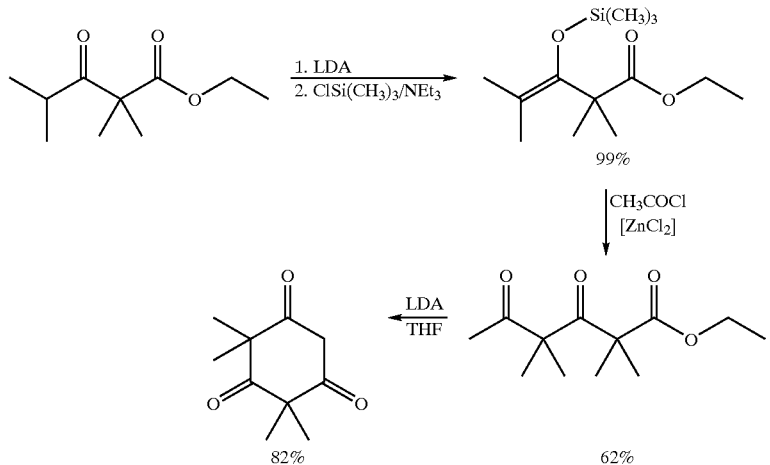

It is furthermore known that

4. Silyl ketene acetals rearrange under thermal stress to give silyl enol ethers. If the silyl ketene acetal of methyl isobutyrate is thermolyzed at 200° C. without solvent, methyl 2,4,4-trimethyl-3-(trimethylsilyloxy)-pent-2-enecarboxylate is obtained in 75% yield. 2,2,4,4-Tetramethyl-1,3-cyclobutadiene, inter alia, is formed as a by-product (C. Ainsworth et al., J. Orgmetal. Chem. 46 (1972) 59).

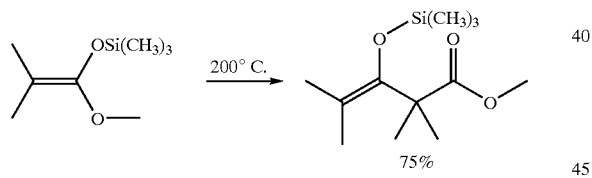

Both the first and the second abovementioned synthesis route yield 2,2,4,4-tetramethyl-1,3,5-cyclohexanetrione in unsatisfactory yields. Moreover, toxic dimethylcadmium is employed in the multistage 2$^{nd}$ reaction sequence.

In the 3$^{rd}$ synthesis variant, two equivalents of base are needed for the preparation of the silyl ether. The reaction must furthermore be carried out at low temperatures (−78° C.), so that this process is also problematical from technical points of view.

The preparation of methyl 2,4,4-trimethyl-3-(trimethylsilyloxy)-pent-2-enecarboxylate according to sequence 4 necessitates working in a bomb tube—this is laborious, complicated and relatively expensive. Moreover, the silyl ketene acetals needed are laborious to prepare.

As a consequence, these synthesis routes can be unsatisfactory as economical and efficient processes for the preparation of 2,2,4-tetrasubstituted 1,3,5-cyclohexanetriones.

It is an object of the present invention, therefore, to find an alternative synthesis process for the preparation of 2,2, 4,4-tetrasubstituted 1,3,5-cyclohexanetriones, which does not have the abovementioned disadvantages of the preparation methods known until now.

We have found that this object is achieved by the process according to the invention for the preparation of 2,2,4,4-tetrasubstituted 1,3,5-cyclohexanetriones of the formula I

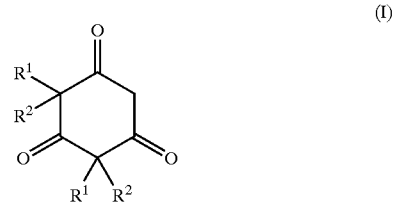

in which

R$^1$, R$^2$, are C$_1$–C$_6$-alkyl or C$_3$–C$_6$-cycloalkyl, where these two radicals can be unsubstituted or partially or completely halogenated and/or substituted by the following radicals:

C$_1$–C$_4$-alkoxy, C$_1$–C$_4$-alkylthio or di(C$_1$–C$_4$-alkyl)amino;

C$_1$–C$_6$-alkoxy, C$_2$–C$_6$-alkenyl or C$_2$–C$_6$-alkynyl;

aryl, aryloxy or heterocyclyl, which has up to three heteroatoms from the group consisting of O, S and N, where the aryl, the aryloxy and the heterocyclyl radical can be unsubstituted or partially or completely halogenated and/or substituted by the following radicals: C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;

or two radicals R$^1$ and R$^2$, which are bonded to the same carbon, together form a —(CH$_2$)$_{2-6}$— chain, which can be substituted by the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;

which comprises a) reacting a cyclobutane-1,3-dione of the formula II

II where $R^1$ and $R^2$ have the abovementioned meanings, with an O or N nucleophile, if appropriate in the presence of a base, and a silylating reagent to give the silyl enol ether of the formula III,

III where $R^3$ is $C_1$–$C_8$-alkoxy, amino, $C_1$–$C_6$-alkylamino or di($C_1$–$C_6$-alkyl)amino;

$R^4$ is $C_1$–$C_6$-alkyl or phenyl;

$R^1$ and $R^2$ have the abovementioned meanings;

b) converting the compound III by acetylation, if appropriate in the presence of a Lewis acid, into the tricarbonyl compound of the formula IV,

IV where $R^1$ to $R^3$ have the abovementioned meanings;

c) cyclizing the compound IV in the presence of a base to give the 2,2,4,4-tetrasubstituted cyclohexanetrione of the formula I.

The reaction sequence for the preparation of the 2,2,4,4-tetrasubstituted 1,3,5-cyclohexanetriones of the formula I is compiled in the following scheme:

Scheme 1:

In what follows, the individual reaction stages and preferred embodiments are explained in greater detail. The preferred embodiments of the individual reaction stages apply not only on their own but also in combination with the other process stages:

Stage a):

In this reaction, suitable O nucleophiles are $C_1$–$C_8$-alcohols, such as methanol, ethanol, 1-propanol, 2-propanol, 1-butanol, 2-butanol, 2-methylpropan-1-ol, 2-methylpropan-2-ol, 1-pentanol, 2-pentanol, 3-pentanol, 2-methylbutan-1-ol, 3-methylbutan-1-ol, 1,1-dimethylpropan-1-ol, 1,2-dimethylpropan-1-ol, 2,2-dimethylpropan-1-ol, 1-hexanol, 2-hexanol, 3-hexanol or 2-ethylhexanol.

Suitable N nucleophiles are ammonia, $C_1$–$C_6$-alkylamines, such as methylamine, ethylamin, 1-propylamine, 2-propylamine, 1-butylamine, 2-butylamine, 2-methylprop-1-ylamine, 2-methylprop-2-ylamine, 1-pentylamine, 2-pentylamine, 3-pentylamine, 2-methylbut-1-ylamine, 3-methylbut-1-ylamine, 1,1-dimethylprop-1-ylamine, 1,2-dimethylprop-1-ylamine, 2,2-dimethylprop-1-ylamine, 1-hexylamine, 2-hexylamine or 3-hexylamine or di($C_1$–$C_6$-alkyl)amines such as dimethylamine, diethylamine, di(1-propyl)amine, di(2-propyl)amine, di(1-butyl)amine, di(2-butylamine), di(2-methylprop-1-yl)amine, di(2-methylprop-2-yl)amine, di(1-pentylamine), di(2-pentyl)amine, di(3-pentylamine), di(2-methylbut-1-yl)amine, di(3-methylbut-1-yl)amine, di(1,1-dimethylprop-1-yl)amine, di(1,2-dimethylprop-1-yl)amine, di(2,2-dimethylprop-1-yl)amine, di(1-hexyl)amine, di(2-hexyl)amine, di(3-hexyl)amine, N-methyl-N-ethylamine, N-methyl-N-1-propylamine, N-methyl-N-2-propylamine, N-methyl-N-1-butylamine, N-methyl-N-2-butylamine, N-methyl-N-2-methylprop-1-ylamine, N-methyl-N-2-methylprop-2-ylamine, N-methyl-N-pentylamine, N-methyl-N-2-pentylamine, N-methyl-N-3-pentylamine, N-methyl-N-2-methylbut-1-ylamine, N-methyl-N-3-methylbut-1-ylamine, N-methyl-N-1,1-dimethylprop-1-ylamine, N-methyl-N-1,2-dimethylprop-1-ylamine, N-methyl-N-2,2-dimethylprop-1-ylamine, N-methyl-N-1-hexylamine, N-methyl-N-2-hexylamine, N-methyl-N-3-hexylamine, N-ethyl-N-2-propylamine, N-ethyl-N-2-propylamine, N-ethyl-N-1-butylamine, N-ethyl-N-2-butylamine, N-ethyl-N-2-methylprop-1-ylamine, N-ethyl-N-2-methylprop-2-ylamine, N-ethyl-N-pentylamine, N-ethyl-N-2-pentylamine, N-ethyl-N-3-pentylamine, N-ethyl-N-2-methylbut-1-ylamine, N-ethyl-N-3-methylbut-1-ylamine, N-ethyl-N-1,1-dimethylprop-1-ylamine, N-ethyl-N-1,2-dimethylprop-1-ylamine, N-ethyl-N-2,2-dimethylprop-1-ylamine, N-ethyl-N-1-hexylamine, N-ethyl-N-2-hexylamine or N-ethyl-N-3-hexylamine.

Likewise, the alkali metal or alkaline earth metal salts of the $C_1$–$C_8$-alcohols, $C_1$–$C_6$-alkylamines or di($C_1$–$C_6$-alkyl) amines and of ammonia are suitable, i.e., for example, the lithium, sodium, potassium, magnesium or calcium salts.

If $C_1$–$C_8$-alcohols, ammonia, $C_1$–$C_6$-alkylamine or di($C_1$–$C_6$-alkyl)amine are employed as O or N nucleophiles, it may be advantageous to employ a base. Suitable bases for this are, inter alia, hydrides such as sodium hydride or potassium hydride, carbonates such as sodium carbonate, potassium carbonate, hydrogencarbonates such as sodium hydrogencarbonate or potassium hydrogencarbonate or amine bases such as triethylamine, pyridine, etc.

Preferred O or N nucleophiles are alkali metal alcoholates, such as sodium methanolate, sodium ethanolate, sodium 1-propanolate, sodium 2-propanolate, sodium 1-butanolate, sodium 2-butanolate, sodium 2-methylpropan-1-olate, sodium 2-methylpropan-2-olate, sodium 2-ethylhexan-1-olate, potassium methanolate, potassium ethanolate, potassium 1-propanolate, potassium 2-propanolate, potassium 1-butanolate, potassium 2-butanolate, potassium 2-methylpropan-1-olate, potassium 2-methylpropan-2-olate or potassium 2-ethylhexan-1-olate or alkaline earth metal alcoholates such as calcium methylate, calcium ethanolate, calcium 1-propanolate, calcium 1-butanolate, magnesium methylate, magnesium ethanolate, magnesium 1-propanolate or magnesium 1-butanolate.

In particular, alkali metal alcoholates such as mentioned above are suitable. Sodium methanolate or sodium ethanolate, in particular sodium methanolate, is particularly preferably employed.

Suitable silylating reagents are alkyl- and/or phenyl-substituted silyl halides, in particular trialkylsilyl halides such as trimethylsilyl chloride, triethylsilyl chloride, trimethylsilyl bromide, trimethylsilyl iodide, tert-butyldimethylsilyl chloride, isopropyldimethylsilyl dichloride, triisopropylsilyl chloride, tri-n-propylsilyl chloride, tri-n-butylsilyl chloride, alkylphenylsilyl halides such as methyldiphenylsilyl chloride, tert-butyldiphenylsilyl chloride or dimethylphenylsilyl chloride, or triphenylsilyl halides such as triphenylsilyl chloride. Trialkylsilyl halides as indicated above are preferably used. Trimethylsilyl chloride, in particular, is suitable.

Preferred cyclobutane-1,3-diones of the formula II are those where $R^1$ is $C_1$–$C_6$-alkyl or $C_3$–$C_6$-cycloalkyl, where these two radicals can be unsubstituted or partially or completely halogenated and/or substituted by the following radicals:

$C_1$–$C_4$-alkoxy, $C_1$–$C_4$-alkylthio or di($C_1$–$C_4$-alkyl)amino; $C_2$–$C_6$-alkenyl or $C_2$–$C_6$-alkynyl;

aryl or heterocyclyl which has up to three heteroatoms from the group consisting of O, S and N, where the aryl and the heterocyclyl radical can be unsubstituted or partially or completely halogenated and/or substituted by the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^2$ is a radical mentioned under $R^1$ and also $C_1$–$C_6$-alkoxy or aryloxy, which can be unsubstituted or partially or completely halogenated and/or substituted by the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

or two radicals $R^1$ and $R^2$, which are bonded to the same carbon, together form a —$(CH_2)_{2-6}$— chain which can be substituted by the following radicals:

halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

Particularly preferred cyclobutane-1,3-diones of the formula II are those where:

$R^1$, $R^2$ are $C_1$–$C_6$-alkyl, which can be unsubstituted or partially or completely halogenated and/or substituted by the following radicals: $C_1$–$C_4$-alkoxy, $C_1$–$C_4$-alkylthio or di($C_1$–$C_4$-alkyl)amino;

or two radicals $R^1$ and $R^2$, which are bonded to the same carbon, together form a —$(CH_2)_{2-6}$— chain, which can be substituted by the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

As a rule, the reaction is carried out in a solvent or diluent. Those suitable for this are, in particular, alcohols such as methanol, ethanol, 1-propanol, 2-propanol, 1-butanol or 2-butanol, ethers such as diethyl ether, diisopropyl ether, tert-butyl methyl ether, dioxane, anisole or tetrahydrofuran, aromatic hydrocarbons such as toluene or xylene or dipolar aprotic solvents such as dimethylformamide or diethylformamide. However, it may also be suitable to use mixtures thereof.

Preferably, the reaction is carried out in alcohols such as methanol, ethanol, 1-propanol, 2-propanol, 1-butanol or 2-butanol or ethers such as diethyl ether, diisopropyl ether, tert-butyl methyl ether, dioxane, anisole or tetrahydrofuran. However, it may also be suitable to use mixtures thereof.

Preferably, the reaction is carried out in an ether such as indicated above or, if an alcoholate is employed as an O nucleophile, in the corresponding alcohol. Ethers such as diethyl ether, methyl tert-butyl ether or tetrahydrofuran are particularly suitable.

As a rule, the 2,2,4,4-tetrasubstituted cyclobutane-1,3-dione, the O or N nucleophile and the silylating reagent are employed in a roughly stoichiometric ratio (0.8:1–1.2:1).

In the case in which a base is added, this is also employed in a roughly stoichiometric ratio (0.8:1–1.2:1) in relation to the compound of the formula II.

It can be advantageous to work with exclusion of water.

The reaction is in general carried out in a temperature range of from 0 to 120° C., in particular from 0 to 60° C.

This reaction is furthermore carried out at a pressure from 1 to 50 bar, preferably at 1 to 10 bar.

Customarily, the cyclobutane-1,3-dione of the formula II and the O/N nucleophile are introduced into a solvent/diluent and the silylating agent is added in the desired temperature range, preferably at room temperature, while guaranteeing thorough mixing. The latter can be added without solvent or in a solvent/diluent. Working-up is carried out in analogy to working-up methods known per se.

Stage b):

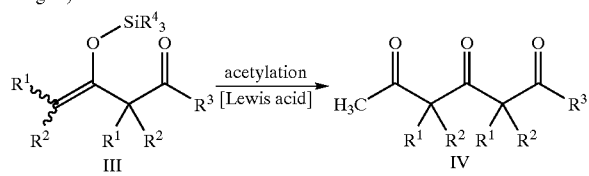

In this reaction, the acetylating reagents used are, for example, acetyl halides such as acetyl chloride or acetyl bromide, acetyl cyanide, mixed anhydrides of acetic acid with inorganic acids, such as methylsulfonic acid or trifluoromethylsulfonic acid, acetylimidazolide or acetic anhydride. Acetyl halides, in particular acetyl chloride, are preferred.

The acetylation takes place in the presence of a Lewis acid. In particular, zinc, aluminum, antimony, titanium, tin, boron, iron, nickel and cobalt halides are employed, preferably the corresponding chlorides or bromides. $ZnCl_2$, $SbCl_3$, $SbCl_5$, $TiCl_4$, $SnCl_4$, $BCl_3$, $FeCl_3$, $AlCl_3$, $AlBr_3$ etc., or mixtures thereof, are particularly suitable. $ZnCl_2$, $AlCl_3$ or $SbCl_3$ are particularly used, particularly preferably $ZnCl_2$.

As a rule, the reaction is carried out in a solvent or diluent. Those suitable for this are, in particular, halogenated hydrocarbons, such as methylene chloride, chloroform, 1,2-dichloroethane or chlorobenzene, or ethers such as diethyl ether, diisopropyl ether, methyl tert-butyl ether, dioxane, tetrahydrofuran or anisole or mixtures thereof. Aliphatic, halogenated hydrocarbons, such as methylene chloride, chloroform or 1,2-dichloroethane or aliphatic/cycloaliphatic ethers such as diethyl ether, diisopropyl ether, methyl tert-butyl ether, dioxane or tetrahydrofuran are preferably used. Methylene chloride or diethyl ether or mixtures thereof are particularly suitable.

Customarily, the silyl enol ether of the formula III and the acetylating reagent are employed in a stoichiometric ratio. However, it can also be advantageous to employ an excess of acetylating reagent. Preferably, the reaction is carried out in a roughly stoichiometric ratio. The acetylating reagent and the Lewis acid are in general employed in the ratio 1:0.1 to 1:2 (molar ratio), preferably a ratio of 1:0.5 to 1:1.5, in particular, for example, a ratio of 1:1.

Preferably, silyl enol ethers of the formula III are employed, where $R^3$ is $C_1-C_8$-alkoxy, in particular methoxy.

Particularly preferably, silyl enol ethers of the formula III are employed, where $R^1$ is $C_1-C_6$-alkyl or $C_3-C_6$-cycloalkyl, where these two radicals can be unsubstituted or partially or completely halogenated and/or substituted by the following radicals:

$C_1-C_4$-alkoxy, $C_1-C_4$-alkylthio or di($C_1-C_4$-alkyl)amino;

$C_2-C_6$-alkenyl or $C_2-C_6$-alkynyl;

aryl or heterocyclyl, which has up to three heteroatoms from the group consisting of O, S and N, where the aryl and the heterocyclyl radical can be unsubstituted or partially or completely halogenated and/or substituted by the following radicals: $C_1-C_4$-alkyl, $C_1-C_4$-haloalkyl, $C_1-C_4$-alkoxy, $C_1-C_4$-haloalkoxy or $C_1-C_4$-alkoxycarbonyl;

$R^2$ is a radical mentioned under $R^1$ and also $C_1-C_6$-alkoxy or aryloxy, which can be unsubstituted or partially or completely halogenated and/or substituted by the following radicals: $C_1-C_4$-alkyl, $C_1-C_4$-haloalkyl, $C_1-C_4$-alkoxy, $C_1-C_4$-haloalkoxy or $C_1-C_4$-alkoxycarbonyl;

or two radicals $R^1$ and $R^2$, which are bonded to the same carbon, together form a —$(CH_2)_{2-6}$— chain which can be substituted by the following radicals: halogen, $C_1-C_4$-alkyl, $C_1-C_4$-haloalkyl, $C_1-C_4$-alkoxy, $C_1-C_4$-haloalkoxy or $C_1-C_4$-alkoxycarbonyl.

Particularly preferably, silyl enol ethers of the formula III are employed, where:

$R^1$, $R^2$ are $C_1-C_6$-alkyl, which can be unsubstituted or partially or completely halogenated and/or substituted by the following radicals: $C_1-C_4$-alkoxy, $C_1-C_4$-alkylthio or di($C_1-C_4$-alkyl)amino;

or two radicals $R^1$ and $R^2$, which are bonded to the same carbon, together form a —$(CH_2)_{2-6}$— chain, which can be substituted by the following radicals: halogen, $C_1-C_4$-alkyl, $C_1-C_4$-haloalkyl, $C_1-C_4$-alkoxy, $C_1-C_4$-haloalkoxy or $C_1-C_4$-alkoxycarbonyl.

In general, the reaction is carried out in a temperature range from −30° C. up to the boiling point of the solvent/solvent mixture. Customarily, it is carried out in a range from −15 to 40° C., preferably with ice-cooling.

This reaction is furthermore carried out at a pressure from 1 to 50 bar, preferably at normal pressure.

Customarily, the acetylating reagent and the Lewis acid are introduced into the solvent/diluent or a corresponding mixture and the silyl enol ether of the formula III is added dropwise without solvent or in a solvent/diluent or a corresponding mixture, the reaction temperature being kept in the desired range, if appropriate, by cooling.

It can be advantageous to work with exclusion of water.

The working-up is carried out in analogy to working-up methods known per se.

Stage c):

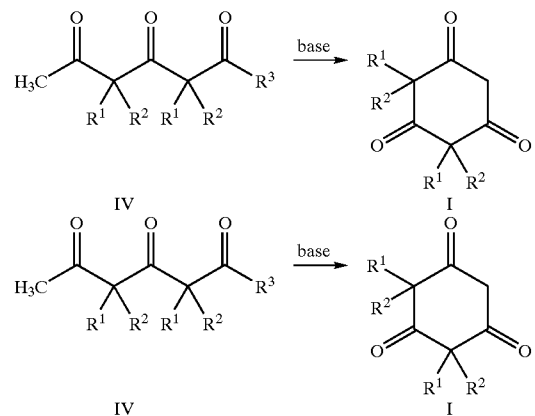

Suitable bases are inorganic and organic bases, and also metal hydrides and organometallic bases.

The bases used in this reaction are inorganic bases such as alkali metal hydroxides, e.g. sodium hydroxide or potassium hydroxide, alkaline earth metal hydroxides, e.g. calcium hydroxide or magnesium hydroxide, alkali metal alcoholates, such as sodium methanolate, sodium ethanolate, sodium 1-propanolate, sodium 2-propanolate, sodium 1-butanolate, sodium 2-butanolate, sodium 2-methylpropan-1-olate, sodium 2-methylpropan-2-olate, sodium 2-ethylhexan-1-olate, potassium methanolate, potassium ethanolate, potassium 1-propanolate, potassium 2-propanolate, potassium 1-butanolate, potassium 2-butanolate, potassium 2-methylpropan-1-olate, potassium 2-methylpropan-2-olate or potassium 2-ethylhexan-1-olate or alkaline earth metal alcoholates such as calcium methylate, calcium ethanolate, calcium 1-propanolate, calcium 1-butanolate, magnesium methylate, magnesium ethanolate, magnesium 1-propanolate or magnesium 1-butanolate, alkali metal oxides, e.g. sodium oxide or potassium oxide, alkaline earth metal oxides, e.g. calcium oxide or magnesium oxide, alkali metal hydrogencarbonates, such as sodium hydrogencarbonate or potassium hydrogencarbonate, alkaline earth metal hydrogencarbonates, such as magnesium hydrogencarbonate or calcium hydrogencarbonate, alkali metal carbonates such as sodium carbonate or potassium carbonate or alkaline earth metal carbonates such as calcium carbonate or magnesium carbonate.

Organic bases, for example amine bases such as trialkylamines, e.g. triethylamine, or aromatic nitrogen bases such as pyridine, are furthermore also suitable.

It is also suitable to employ hydrides such as sodium hydride, potassium hydride or lithium aluminum hydride or organometallic bases such as butyllithium, lithium diisopropylamide etc.

In particular, inorganic bases such as mentioned above are employed, in particular alkali metal hydroxides, alkaline earth metal hydroxides, alkali metal oxides, alkaline earth metal oxides, alkali metal hydrogencarbonates, alkaline earth metal hydrogencarbonates, alkali metal carbonates or alkaline earth metal carbonates, such as described above, preferably alkali metal or alkaline earth metal hydroxides.

In particular, amine bases such as mentioned above, preferably trialkylamines, are also employed.

Particularly preferably, sodium hydroxide is used.

Preferably, tricarbonyl compounds of the formula IV are employed where $R^3$ is $C_1$–$C_8$-alkoxy, in particular methoxy.

Particularly preferably, tricarbonyl compounds of the formula IV are employed where $R^1$ is $C_1$–$C_6$-alkyl or $C_3$–$C_6$-cycloalkyl, where these two radicals can be unsubstituted or partially or completely halogenated and/or substituted by the following radicals: $C_1$–$C_4$-alkoxy, $C_1$–$C_4$-alkylthio or di($C_1$–$C_4$-alkyl)amino;

$C_2$–$C_6$-alkenyl or $C_2$–$C_6$-alkynyl;

aryl or heterocyclyl, which has up to three heteroatoms from the group consisting of O, S and N, where the aryl and the heterocyclyl radical can be unsubstituted or partially or completely halogenated and/or substituted by the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^2$ is a radical mentioned under $R^1$ and also $C_1$–$C_6$-alkoxy or aryloxy, which can be unsubstituted or partially or completely halogenated and/or substituted by the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

or two radicals $R^1$ and $R^2$, which are bonded to the same carbon, together form a —$(CH_2)_{2-6}$— chain which can be substituted by the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

Particularly preferably, tricarbonyl compounds of the formula IV are employed where $R^1$, $R^2$ are $C_1$–$C_6$-alkyl, which can be unsubstituted or partially or completely halogenated and/or substituted by the following radicals: $C_1$–$C_4$-alkoxy, $C_1$–$C_4$-alkylthio or di($C_1$–$C_4$-alkyl)amino; or two radicals $R^1$ and $R^2$, which are bonded to the same carbon, together form a —$(CH_2)_{2-6}$— chain, which can be substituted by the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

As a rule, the reaction is carried out in an inert solvent or diluent. Those suitable for this are, for example, ethers such as diethyl ether, diisopropyl ether, methyl tert-butyl ether, dioxane, tetrahydrofuran or anisole, aromatic hydrocarbons such as benzene or toluene, or aprotic, dipolar solvents such as dimethylformamide or dimethyl sulfoxide or mixtures thereof. Preferably, aliphatic/cycloaliphatic ethers, such as diethyl ether, diisopropyl ether, methyl tert-butyl ether, dioxane or tetrahydrofuran, or aprotic, dipolar solvents such as mentioned above, are used.

Diethyl ether, tetrahydrofuran, dimethylformamide and dimethyl sulfoxide are particularly suitable.

Customarily, the tricarbonyl compound of the formula IV and the base are employed in a ratio of 1:1 to 1:4 (molar ratio), preferably in a ratio of 1:1 to 1:2.5.

If inorganic bases are used, as mentioned above, it can be advantageous to work in roughly a stoichiometric ratio.

The reaction is in general carried out in a temperature range from −75° C. up to the boiling point of the solvent/solvent mixture. Preferably, it is carried out in a temperature range from −30° C. up to the boiling point of the solvent/solvent mixture. When using inorganic bases or amine bases, it is preferably carried out in a range from 0 to 120° C., preferably in a range from 20–100° C.

This reaction is furthermore carried out at a pressure from 1 to 100 bar, preferably at a pressure from 1 to 20 bar, in particular at normal pressure.

As a rule, the base is introduced into the solvent/diluent and the tricarbonyl compound of the formula IV, if appropriate in a solvent/diluent, is added in the desired temperature range while guaranteeing thorough mixing. The working-up is carried out in analogy to working-up processes known per se.

It is furthermore possible to obtain the cyclobutane-1,3-dione of the formula II by reaction of an acid halide of the formula V, where Hal is halide and $R^1$ and $R^2$ have the meanings mentioned in the case of compound I, with a base.

Stage a1)

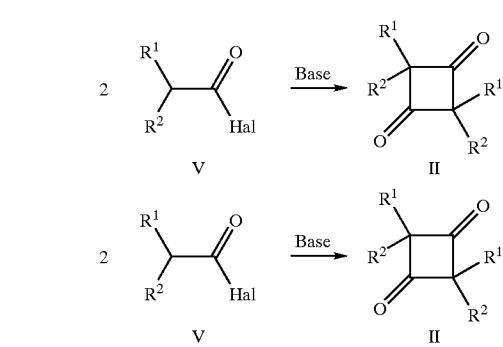

In this reaction, amine bases such as trialkylamines, e.g. triethylamine or aromatic nitrogen bases, e.g. pyridine, are preferably used. Trialkylamines, in particular triethylamine, are preferably employed.

Customarily, the acid halide employed is the chloride or bromine, in particular the acid chloride.

Particularly preferred acid halides of the formula V employed are those where:

$R^1$ is $C_1$–$C_6$-alkyl or $C_3$–$C_6$-cycloalkyl, where these two radicals can be unsubstituted or partially or completely halogenated and/or substituted by the following radicals: $C_1$–$C_4$-alkoxy, $C_1$–$C_4$-alkylthio or di($C_1$–$C_4$-alkyl)amino;

$C_2$–$C_6$-alkenyl or $C_2$–$C_6$-alkynyl;

aryl or heterocyclyl, which has up to three heteroatoms from the group consisting of O, S and N, where the aryl and the heterocyclyl radical can be unsubstituted or partially or completely halogenated and/or substituted by the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^2$ is a radical mentioned under $R^1$ and also $C_1$–$C_6$-alkoxy or aryloxy, which can be unsubstituted or partially or completely halogenated and/or substituted by the following radicals: $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

or two radicals $R^1$ and $R^2$, which are bonded to the same carbon, together form a —$(CH_2)_{2-6}$— chain which can be substituted by the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

Particularly preferred acid halides of the formula V employed are those where:

$R^1$, $R^2$ are $C_1$–$C_6$-alkyl, which can be unsubstituted or partially or completely halogenated and/or substituted by the following radicals: $C_1$–$C_4$-alkoxy, $C_1$–$C_4$-alkylthio or di($C_1$–$C_4$-alkyl)amino;

or two radicals $R^1$ and $R^2$, which are bonded to the same carbon, together form a —$(CH_2)_{2-6}$— chain, which can be substituted by the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl.

As a rule, the reaction is carried out in an inert solvent or diluent. Those suitable are, for example, ethers such as diethyl ether, diisopropyl ether, methyl tert-butyl ether, dioxane, tetrahydrofuran or anisole, glycols, such as diethylene glycol dimethyl ether, aromatic hydrocarbons such as benzene, toluene or xylene or halogenated hydrocarbons such as methylene chloride, chloroform, 1,2-dichloroethane or chlorobenzene, or mixtures thereof. Preferably, aliphatic ethers, such as diethyl ether, diisopropyl ether or methyl tert-butyl ether, glycols, such as diethylene glycol dimethyl ether or aromatic hydrocarbons such as benzene, toluene or xylene are used, in particular methyl tert-butyl ether, diethylene glycol dimethyl ether or toluene.

As a rule, the acid halide of the formula V and the base are employed in the ratio 1:1 to 1:3, preferably in the range from 1:1.5 to 1:2.5.

In general, the reaction is carried out at elevated temperature, in particular in the range of the boiling temperature of the solvent/diluent.

The reaction is furthermore carried out at a pressure from 1 to 100 bar.

Customarily, the acid chloride is introduced into the solvent/diluent and the base, if appropriate, dissolved in a solvent/diluent, is added. The mixture is then warmed to reflux temperature of the solvent/diluent.

The working-up is carried out in analogy to known working-up processes.

Furthermore, it is possible to employ the compounds II, III or IV in the next stage without purification.

Likewise, it is possible to elaborate the stages a) and b) or b) and c) or a1) and a) or a), b) and c) or a1), a) and b) or a1), a), b) and c) as "one-pot processes".

Suitable solvents here are, in particular, ethers such as diethyl ether, methyl tert-butyl ether, tetrahydrofuran or dioxane or dipolar solvents such as dimethyl sulfoxide or mixtures thereof.

Stage a) of the process according to the invention is a novel and advantageous process for the preparation of silyl enol ethers of the formula III. The present invention therefore also relates to the process described in stage a). The preferred embodiments described there accordingly apply.

Furthermore, stage c) of the process according to the invention, if an oxide, hydroxide, hydrogencarbonate or carbonate of an alkali metal or alkaline earth metal is used, is a novel and advantageous process for the preparation of 2,2,4,4-tetrasubstituted cyclohexane-1,3,5-triones of the formula I. This is also a subject of the present invention.

Suitable bases are alkali metal hydroxides, such as sodium hydroxide or potassium hydroxide, alkaline earth metal hydroxides, such as calcium hydroxide or magnesium hydroxide, alkali metal oxides such as sodium oxide or potassium oxide, alkaline earth metal oxides, such as calcium oxide or magnesium oxide, alkali metal hydrogencarbonates, such as sodium hydrogencarbonate or potassium hydrogencarbonate, alkaline earth metal hydrogencarbonates, such as magnesium hydrogencarbonate or calcium hydrogencarbonate, alkali metal carbonates such as sodium carbonate or potassium carbonate or alkaline earth metal carbonates such as calcium carbonate or magnesium carbonate.

Alkali metal or alkaline earth metal hydroxides, such as sodium, potassium, calcium or magnesium hydroxide, are preferably employed.

Sodium hydroxide is particularly preferably used.

As a rule, the reaction is carried out in an inert solvent or diluent. Those suitable for this are, for example, ethers such as diethyl ether, diisopropyl ether, methyl tert-butyl ether, dioxane, tetrahydrofuran or anisole or aprotic solvents such as dimethylformamide or dimethyl sulfoxide, or mixtures thereof.

Aliphatic/cycloaliphatic ethers such as diethyl ether, diisopropyl ether, methyl tert-butyl ether, dioxane or tetrahydrofuran, or aprotic, dipolar solvents such as mentioned above, are preferably used.

Diethyl ether, tetrahydrofuran and dimethyl sulfoxide are particularly suitable.

Customarily, the tricarbonyl compounds of the formula IV and the base are employed in the ratio 1:1 to 1:4 (molar ratio), preferably in the ratio 1:1 to 1:2.5. It can be advantageous to work in roughly a stoichiometric ratio.

The reaction is in general carried out in a temperature range from –75° C. up to the boiling point of the solvent/solvent mixture. Preferably, it is carried out in a range from –30° C. up to the boiling point of the solvent/solvent mixture, particularly in the range from 0 to 120° C., in particular 20–100° C. Otherwise, the embodiments mentioned under stage c) apply.

Furthermore, stage c) of the process according to the invention, if the base used is an alkali metal or alkaline earth metal alcoholate in the ratio 1:1 to 1:3 (compound IV:base; molar ratio), is a novel and advantageous process for the preparation of 2,2,4,4-tetrasubstituted cyclohexane-1,3,5-triones of the formula I.

Suitable alkali metal or alkaline earth metal alcoholates are alkali metal alcoholates such as sodium methanolate, sodium ethanolate, sodium 1-propanolate, sodium 2-propanolate, sodium 2-butanolate, sodium 2-methylpropan-1-olate, sodium 2-methylpropan-2-olate, sodium 2-ethylhexan-1-olate, potassium methanolate, potassium ethanolate, potassium 1-propanolate, potassium 2-propanolate, potassium 1-butanolate, potassium 2-butanolate, potassium 2-methylpropan-1-olate, potassium 2-methylpropan-2-olate or potassium 2-ethylhexan-1-olate or alkaline earth metal alcoholates such as calcium methanolate, calcium ethanolate, calcium 1-propanolate, calcium 1-butanolate, magnesium methylate, magnesium methanolate, magnesium 1-propanolate or magnesium 1-butanolate.

In particular, alkali metal alcoholates such as mentioned above are used. Sodium methanolate, sodium ethanolate or potassium 2-methylpropan-2-olate are preferably employed.

As a rule, the reaction is carried out in an inert solvent or diluent. Those suitable are, for example, ethers such as diethyl ether, diisopropyl ether, methyl tert-butyl ether, dioxane, tetrahydrofuran or anisole or aprotic solvents such as dimethyl sulfoxide or mixtures thereof.

Aliphatic or cycloaliphatic ethers such as diethyl ether, diisopropyl ether, methyl tert-butyl ether, dioxane or tetrahydrofuran are preferably used. Diethyl ether and tetrahydrofuran are particularly suitable.

Customarily, the tricarbonyl compound of the formula IV and the alkali metal or alkaline earth metal alcoholate are employed in the ratio 1:1 to 1:3 (molar ratio), preferably in the ratio 1:1 to 1:2.5.

The reaction is in general carried out in a temperature range from −75° C. up to the boiling point of the solvent/solvent mixture. Preferably, it is carried out in a range from −30° C. to boiling temperature, in particular at 20–100° C.

Otherwise, the embodiments mentioned under stage c) apply.

The present invention further relates to the novel 2,2,4, 4-tetrasubstituted 1,3,5-cyclohexanetriones of the formula I',

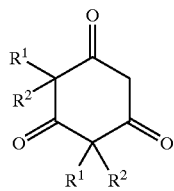

I' where
R$^1$ and R$^2$, which are bonded to the same carbon, form a —(CH$_2$)$_{2-6}$— chain which can be substituted by the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl.

The compounds of the formula I are particularly preferred where R$^1$ and R$^2$, which are bonded to the same carbon, form a —(CH$_2$)$_{2-6}$— chain.

The present invention likewise relates to the novel silyl enol ethers of the formula III',

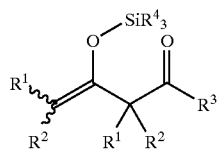

III' where the variables have the following meanings:
R$^1$, R$^2$ are C$_1$–C$_6$-alkyl or C$_3$–C$_6$-cycloalkyl, where these two radicals can be unsubstituted or partially or completely halogenated and/or substituted by the following radicals: C$_1$–C$_4$-alkoxy, C$_1$–C$_4$-alkylthio or di(C$_1$–C$_4$-alkyl)amino; C$_1$–C$_6$-alkoxy, C$_2$–C$_6$-alkenyl or C$_2$–C$_6$-alkynyl; aryl, aryloxy or heterocyclyl, which has up to three heteroatoms from the group consisting of O, S and N, where the aryl, the aryloxy and the heterocyclyl radical can be unsubstituted or partially or completely halogenated and/or substituted by the following radicals: C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;
or two radicals R$^1$ and R$^2$, which are bonded to the same carbon, together form a —(CH$_2$)$_{2-6}$— chain which can be substituted by the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;
R$^3$ is amino, C$_1$–C$_6$-alkylamino or di(C$_1$–C$_6$-alkyl)amino;

R$^4$ is C$_1$–C$_6$-alkyl or phenyl.

Particularly preferred compounds of the formula III' are those where R$^3$ is di(C$_1$–C$_6$-alkyl)amino.

The present invention furthermore relates to the novel tricarbonyl compounds of the formula IV',

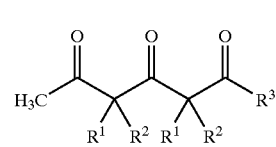

IV' where the variables have the following meanings:
R$^1$, R$^2$ is C$_1$–C$_6$-alkyl or C$_3$–C$_6$-cycloalkyl, where these two radicals can be unsubstituted or partially or completely halogenated and/or substituted by the following radicals: C$_1$–C$_4$-alkoxy, C$_1$–C$_4$-alkylthio or di(C$_1$–C$_4$-alkyl)amino;
C$_1$–C$_6$-alkoxy, C$_2$–C$_6$-alkenyl or C$_2$–C$_6$-alkynyl;
aryl, aryloxy or heterocyclyl, which has up to three heteroatoms from the group consisting of O, S and N, where the aryl, the aryloxy and the heterocyclyl radical can be unsubstituted or partially or completely halogenated and/or substituted by the following radicals: C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;
or two radicals R$^1$ and R$^2$, which are bonded to the same carbon, together form a —(CH$_2$)$_{2-6}$— chain which can be substituted by the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;
R$^3$ is amino, C$_1$–C$_6$-alkylamino or di(C$_1$–C$_6$-alkyl)amino.

Particularly preferred compounds of the formula IV' are those where R$^3$ is di(C$_1$–C$_6$-alkyl)amino.

The present invention also relates to the novel tricarbonyl compounds of the formula IV",

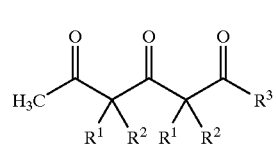

IV"

where R$^1$ and R$^2$, which are bonded to the same carbon, form a —(CH$_2$)$_{2-6}$— chain which can be substituted by the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;
R$^3$ is C$_1$–C$_8$-alkoxy.

Particularly preferred compounds of the formula IV" are those where R$^1$ and R$^2$, which are bonded to the same carbon, form a —(CH$_2$)$_{2-6}$— chain.

The organic entities mentioned for the substituents R$^1$ to R$^4$ or as radicals on phenyl or heterocyclyl radicals are collective concepts of individual lists of the separate group members. All hydrocarbon chains, i.e. all alkyl, haloalkyl, alkoxy, haloalkoxy, alkylthio, alkylamino, dialkylamino or alkoxycarbonyl moieties can be straight-chain or branched. If not stated otherwise, halogenated substituents preferably carry one to five identical or different halogen atoms. The meaning of halogen is in each case fluorine, chlorine, bromine or iodine.

Furthermore, the following are, for example:
C$_1$–C$_4$-alkyl: e.g. methyl, ethyl, propyl, 1-methylethyl, butyl, 1-methylpropyl, 2-methylpropyl or 1,1-dimethylethyl;

$C_1$–$C_6$-alkyl, $C_1$–$C_4$-alkyl, as mentioned above, and also, for example, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl or 1-ethyl-3-methylpropyl;

$C_1$–$C_4$-haloalkyl: a $C_1$–$C_4$-alkyl radical, as mentioned above, which is partially or completely substituted by fluorine, chlorine, bromine and/or iodine, i.e., for example, chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl or nonafluorobutyl;

$C_1$–$C_4$-alkoxy: e.g. methoxy, ethoxy, propoxy, 1-methylethoxy, butoxy, 1-methylpropoxy, 2-methylpropoxy or 1,1-dimethylethoxy;

$C_1$–$C_6$-alkoxy: $C_1$–$C_4$-alkoxy, as mentioned above, and also, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy;

$C_1$–$C_8$-alkoxy: $C_1$–$C_6$-alkoxy, as mentioned above and also 1-heptoxy, 1-octoxy or 2-ethylhexoxy;

$C_1$–$C_4$-haloalkoxy: a $C_1$–$C_4$-alkoxy radical, as mentioned above, which is partially or completely substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy or nonafluorobutoxy;

$C_1$–$C_4$-alkylthio: e.g. methylthio, ethylthio, propylthio, 1-methylethylthio, butylthio, 1-methylpropylthio, 2-methylpropylthio or 1,1-dimethylethylthio;

$C_1$–$C_6$-alkylamino: e.g. methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$–$C_4$-alkyl)amino: e.g. N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-Ethyl-N-(2-methylpropyl) amino, N-Ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino or N-(1,1-dimethylethyl)-N-(2-methylpropyl)amino;

di($C_1$–$C_6$-alkyl)amino: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

$C_2$–$C_6$-alkenyl: e.g. ethenyl, prop-2-en-1-yl, but-1-en-4-yl, 1-methylprop-2-n-1-yl, 2-methylprop-2-en-1-yl, 2-buten-1-yl, 1-penten-3-yl, 1-penten-4-yl, 2-penten-4-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-2-en-1-yl, 1-ethylprop-2-en-1-yl, hex-3-en-1-yl, hex-4-en-1-yl, hex-5-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-2-en-1-yl, 1,2-dimethylbut-3-en-1-yl, 1,3-dimethylbut-2-en-1-yl, 1,3-dimethylbut-3-en-1-yl, 2,2-dimethylbut-3-en-1-yl, 2,3-dimethylbut-2-en-1-yl, 2,3-dimethylbut-3-en-1-yl, 3,3-dimethylbut-2-en-1-yl, 1-ethylbut-2-en-1-yl, 1-ethylbut-3-n-1-yl, 2-ethylbut-2-en-1-yl, 2-ethylbut-3-en-1-yl, 1,1,2-trimethylprop-2-en-1-yl, 1-ethyl-1-methylprop-2-en-1-yl or 1-ethyl-2-methylprop-2-en-1-yl;

$C_2$–$C_6$-alkynyl: e.g. ethynyl, propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_3$–$C_6$-cycloalkyl: e.g. cyclopropyl, cyclobutyl, cyclopentyl or cyclohexyl;

aryl: e.g. phenyl or naphthyl;

heterocyclyl: a saturated, partially saturated or unsaturated 5- or 6-membered, C-bonded, heterocyclic ring, which contains one to four identical or different heteroatoms, selected from the following group: oxygen, sulfur or nitrogen, i.e., for example, 5-membered rings having, for example, one heteroatom, having two heteroatoms, having three heteroatoms or having four heteroatoms or, for example, 6-membered rings having, for example, one heteroatom, having two heteroatoms, having three heteroatoms or having four heteroatoms, i.e.

5-membered rings having one heteroatom such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 4,5-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 2-furyl, 3-furyl, 2-thienyl, 3-thienyl, pyrrol-2-yl or pyrrol-3-yl;

5-membered rings having two heteroatoms such as:

tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl or thiazol-5-yl;

5-membered ring having three heteroatoms such as:

1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-oxadiazolin-2-yl, 1,2,3-$\Delta^2$-thiadiazolin-4-yl, 1,2,3-$\Delta^2$-thiadiazolin-5-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,3,2-dioxathiolan-4-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxidiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl or 1,2,4-triazol-3-yl;

5-membered rings having four heteroatoms such as:

tetrazol-5-yl;

6-membered rings having one heteroatom such as:

tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydropyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, pyridin-2-yl, pyridin-3-yl or pyridin-4-yl;

6-membered rings having two heteroatoms such as:
1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-3-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl, pyridazin-3-yl, pyridazin-4-yl, pyrimidin-2-yl, pyrimidin-4-yl, pyrimidin-5-yl or pyrazin-2-yl;

6-membered rings having three heteroatoms such as:
1,3,5-triazin-2-yl, 1,2,4-triazin-3-yl, 1,2,4-triazin-5-yl, 1,2,4-triazin-6-yl;

6-membered rings having four heteroatoms such as:
1,2,4,5-tetrazin-3-yl;

where, if appropriate, the sulfur of the heterocycles mentioned can be oxidized to S=O or S(=O)$_2$.

PREPARATION EXAMPLES 1. 2,2,4,4-Tetramethyl-1,3-cyclobutanedione 172 g (1.7 mol) of triethylamine were added dropwise to a solution of 106 g (1 mol) of isobutyryl chloride in 800 ml of tert-butyl methyl ether and the mixture was then heated under reflux for 15 h. It was washed with dil. hydrochloric acid, the phases were separated and the org. solvent was removed.

Yield: 55 g (78%). $^1$H-NMR (CDCl$_3$): δ=1.3 (s, 12H).

Methyl 2,2,4-Trimethyl-3-silyloxypent-3-enecarboxylate 84 g (0.6 mol) of 2,2,4,4-tetramethylcyclobutane-1,3-dione and 32.4 g (0.6 mol) of sodium methylate were mixed together in 320 ml of tetrahydrofuran. 65.1 g (0.6 mol) of trimethylsilyl chloride were added dropwise and the mixture was stirred. The reaction mixture was then concentrated and the residue was taken up with diethyl ether. The solid was filtered off with suction and the mother liquor was concentrated. Yield: 135 g (89%).

$^1$H-NMR (CDCl$_3$): δ=0.3 (s, 9H), 1.3 (s, 6H), 1.5 (s, 3H), 1.7 (s, 3H), 3.6 (s, 3H).

Methyl 2,2,4,4-tetramethyl-3,5-dioxohexanoate 20 g (82 mmol) of methyl 2,2,4-trimethyl-3-silyloxypent-3-enecarboxylate were added dropwise with ice-cooling to a mixture of 11.2 g (82 mmol) of zinc chloride, 6.45 g (82 mmol) of acetyl chloride in dichloromethane and diethyl ether. The mixture was allowed to warm to room temperature, ice water was added dropwise and the phases were separated. 13.6 g (78%) of methyl 2,2,4,4-tetramethyl-3,5-dioxohexanoate were thus obtained.

$^1$H-NMR (CDCl$_3$): δ=1.3 (s, 6H), 1.4 (s, 6H), 2.1 (s, 3H), 4.6 (s, 3H).

2,2,4,4-Tetramethyl-1,3,5-cyclohexanetrione 106 g (495 mmol) of methyl 2,2,4,4-tetramethyl-3,5-dioxohexanoate were added dropwise to a suspension of 19.8 g (495 mmol) of sodium hydroxide in 500 ml of dimethyl sulfoxide. The mixture was stirred at room temperature, treated with 500 ml of water and adjusted to pH 1 using hydrochloric acid, and the deposited precipitate was then filtered off with suction. After drying, 70 g (95%) of 2,2,4,4-tetramethyl-1,3,5-cyclohexanetrione were obtained.

$^1$H-NMR (CDCl$_3$): δ=1.3 (s, 12H), 5.4 (s, 1H), 12 (br., OH).

2. Biscyclohexane-1-spiro-2',4'-cyclobutane-1,3-dione

A solution of 100 g (0.68 mol) of cyclohexanecarbonyl chloride and 117 g (1.156 mol) of triethylamine in 800 ml of toluene was heated under reflux for 21 hours. The precipitated solid was subsequently filtered off with suction; this was then washed with water. After drying, 77 g of biscyclohexane-1-spiro-2',4'-cyclobutane-1,3-dione were obtained.

$^1$H-NMR (CDCl$_3$): δ=1.4 (m, 4H), 1.6 (m, 8H), 1.8 (m, 8H).

Silylation of Biscyclohexane-1-spiro-2',4'-cyclobutane-1,3-dione 20.6 g (189 mmol) of chlorotrimethylsilane were added to a suspension of 41.7 g (189 mmol) of biscyclohexane-1-spiro-2',4'-cyclobutane-1,3-dione and 10.3 g (189 mmol) of sodium methylate in 100 ml of tetrahydrofuran. The mixture was stirred at room temperature for 18 hours and filtered off with suction through silica gel. The mother liquor was concentrated and 32 g (51%) of the silylation product were obtained.

$^1$H-NMR (CDCl$_3$): δ=0 (s, 9H), 0.9–1.9 (m, 20H), 3.4 (s, 3H).

Biscyclohexane-1-spiro-2',4'-(Methyl 3,5-Dioxohexanoate)

10.4 g (46 mmol) of the silyl compound described above were added dropwise with ice-cooling to a suspension of 6.3 g (46 mmol) of zinc chloride and 3.61 g (46 mmol) of acetyl chloride in 46 ml of dichloromethane and 12 ml of diethyl ether, then the mixture was stirred at room temperature for 2 hours. It was treated with water and the phases were separated. The organic phase yielded 13.2 g of biscyclohexane-1-spiro-2',4'-(methyl 3,5-dioxohexanoate), which was directly reacted further.

Biscyclohexane-1-spiro-2',4'-cyclohexane-1,3,5-trione

A solution of 2.86 g of biscyclohexane-1-spiro-2',4'-(methyl 3,5-dioxohexanoate) in tetrahydrofuran was added dropwise to a solution of 2.5 g (22 mmol) of potassium tert-butylate in 25 ml of tetrahydrofuran and the mixture was stirred at room temperature for 4 hours. It was adjusted to pH 1 using hydrochloric acid and extracted with dichloromethane. The combined organic phases were dried and the solvent was removed, 2.5 g (95%) of biscyclohexane-1-spiro-2',4'-cyclohexane-1,3,5-trione being obtained.

$^1$H-NMR (CDCl$_3$): δ=1.1–1.9 (m, 20H), 3.4 (s, 2H).

We claim:

1. A process for the preparation of 2,2,4,4-tetrasubstituted 1,3,5-cyclohexanetriones of the formula I

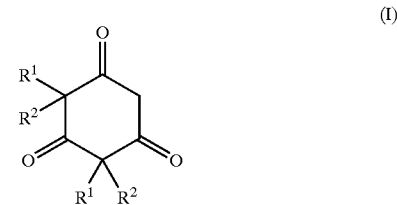

in which

R$^1$, R$^2$ are C$_1$–C$_6$-alkyl or C$_3$–C$_6$-cycloalkyl, where these two radicals are unsubstituted or partially or completely halogenated and/or substituted by the following radicals: C$_1$–C$_4$-alkoxy, C$_1$–C$_4$-alkylthio or di(C$_1$–C$_4$-alkyl)amino;

C$_1$–C$_6$-alkoxy, C$_2$–C$_6$-alkenyl or C$_2$–C$_6$-alkynyl;

aryl, aryloxy or heterocyclyl, which has up to three heteroatoms from the group consisting of O, S and N, where the aryl, the aryloxy and the heterocyclyl radical are unsubstituted or partially or completely halogenated and/or substituted by the following radicals:

C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;

or two radicals R$^1$ and R$^2$, which are bonded to the same carbon, together form a —(CH$_2$)$_{2-6}$— chain, which is optionally substituted by the following radicals: halogen, C$_1$–C$_4$-alkyl, C$_1$–C$_4$-haloalkyl, C$_1$–C$_4$-alkoxy, C$_1$–C$_4$-haloalkoxy or C$_1$–C$_4$-alkoxycarbonyl;

which comprises a) reacting a cyclobutane-1,3-dione of the formula II

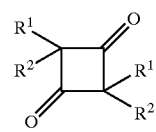

where

R$^1$ and R$^2$ have the abovementioned meanings, with an O or N nucleophile, optionally in the presence of a base, and a silylating reagent to give the silyl enol ether of the formula III

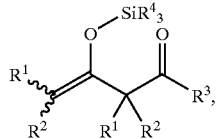

where
- $R^3$ is $C_1$-$C_8$-alkoxy, amino, $C_1$-$C_6$-alkylamino or di($C_1$-$C_6$-alkyl)amino;
- $R^4$ is $C_1$-$C_6$-alkyl or phenyl;
- $R^1$ and $R^2$ have the abovementioned meanings;

b) converting the compound III by acetylation, optionally in the presence of a Lewis acid, into the tricarbonyl compound of the formula IV,

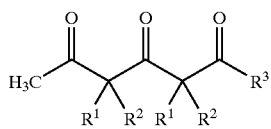

where
- $R^1$ to $R^3$ have the abovementioned meanings;

c) cyclizing the compound IV in the presence of a base to give the 2,2,4,4-tetrasubstituted cyclohexanetrione of the formula I.

2. The process for the preparation of 2,2,4,4-tetrasubstituted 1,3,5-cyclohexanetriones of the formula I as claimed in claim 1, where the cyclobutane-1,3-dione of the formula II is obtained by a1) reaction of an acid halide of the formula V

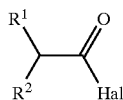

where Hal is halogen and $R^1$ and $R^2$ have the meaning mentioned in claim 1, with a base.

3. The process as claimed in claim 1, wherein in stage a) the cyclobutane-1,3-dione of the formula II is reacted with an alkali metal or alkaline earth metal salt of a $C_1$-$C_6$-alcohol, $C_1$-$C_6$-alkylamine, di($C_1$-$C_6$-alkyl)amine or ammonia.

4. The process as claimed in claim 1, wherein in stage a) the cyclobutane-1,3-dione of the formula II is reacted with an alkali metal or alkaline earth metal alcoholate.

5. The process as claimed in claim 1, wherein in stage a) the cyclobutane-1,3-dione of the formula II is reacted with sodium methanolate.

6. The process as claimed in claim 1, wherein in stage a) ethers or alcohols are used as solvents.

7. The process as claimed in claim 1, wherein the reaction described in stage a) is carried out in a temperature range from 0 to 120° C.

8. The process as claimed in claim 1, wherein an inorganic or organic base is used in stage c).

9. The process as claimed in claim 1, wherein in stage c) the base used is an oxide, hydroxide, alcoholate, hydrogencarbonate or carbonate of an alkali metal or alkaline earth metal.

10. The process as claimed in claim 1, wherein in stage c) the base used is an oxide, hydroxide, hydrogencarbonate or carbonate of an alkali metal or alkaline earth metal.

11. The process as claimed in claim 1, wherein in stage c) the base used is an amine base.

12. The process as claimed in claim 1, where in stage c) the solvents used are ethers, alcohols or aprotic dipolar solvents.

13. The process as claimed in claim 1, wherein the reaction described in stage c) is carried out in a temperature range from 0 to 120° C.

14. A process for the preparation of silyl enol ethers of the formula III, wherein the radicals $R^1$ to $R^4$ have the meanings indicated in claim 1 which comprises reacting a cyclobutane-1,3-dione of formula II, wherein $R^1$ and $R^2$ have the meanings given in claim 1 with an O or N nucleophile and a silylating reagent, optionally in the presence of a base.

15. A process for the preparation of 2,2,4,4-tetrasubstituted 1,3,5-cyclohexanetriones of the formula I wherein the radicals $R^1$ and $R^2$ have the meanings indicated in claim 1, which comprises cyclizing a compound of formula IV wherein $R^1$ to $R^3$ have the meanings given in claim 1 in the presence of a base which is selected from the group oxide, hydroxide, hydrogen carbonate or carbonate of an alkali metal or alkaline earth metal.

16. The process of claim 15, wherein the base used is an alkali metal or alkaline earth metal alcoholate in the ratio 1:1 to 1:3.

17. The process as claimed in claim 16, wherein an ether is used as solvent.

18. The process as claimed in claim 16, wherein the reaction is carried out in a solvent or solvent mixture at a temperature of from −75° C. up to the boiling point of the solvent/solvent mixture.

19. A 2,2,4,4-tetrasubstituted 1,3,5-cyclohexanetrione of the formula I'

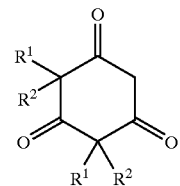

in which $R^1$ and $R^2$, which are bonded to the same carbon, form a —$(CH_2)_{2-6}$— chain optionally substituted by the following radicals:

halogen, $C_1$-$C_4$-alkyl, $C_1$-$C_4$-haloalkyl, $C_1$-$C_4$-alkoxy, $C_1$-$C_4$-haloalkoxy or $C_1$-$C_4$-alkoxycarbonyl.

20. A silyl enol ether of the formula III'

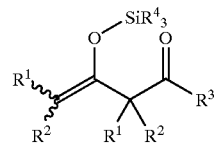

where the variables $R^1$, $R^2$ and $R^4$ have the meanings mentioned in claim 1 and $R^3$ is amino, $C_1$–$C_6$-alkylamino or di($C_1$–$C_6$-alkyl)amino.

21. A tricarbonyl compound of the formula IV'

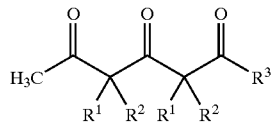

IV' where the variables $R^1$ to $R^3$ have the meanings mentioned in claim 20.

22. A tricarbonyl compound of the formula IV"

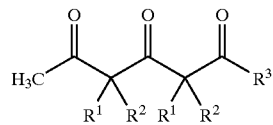

IV"

where $R^1$ and $R^2$, which are bonded to the same carbon, form a —$(CH_2)_{2-6}$— chain optionally be substituted by the following radicals:

halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkoxycarbonyl;

$R^3$ is $C_1$–$C_8$-alkoxy.

* * * * *